United States Patent
Kumon et al.

(10) Patent No.: US 9,222,107 B2
(45) Date of Patent: Dec. 29, 2015

(54) REIC-EXPRESSING ADENOVIRUS VECTOR

(75) Inventors: Hiromi Kumon, Okayama (JP); Namho Huh, Okayama (JP); Masakiyo Sakaguchi, Okayama (JP); Masami Watanabe, Okayama (JP)

(73) Assignees: National University Corporation Okayama University, Okayama (JP); Momotaro-Gene Inc., Okayama (JP)

( * ) Notice: Subject to any disclaimer, the term of this patent is extended or adjusted under 35 U.S.C. 154(b) by 0 days.

(21) Appl. No.: 14/119,772

(22) PCT Filed: May 25, 2012

(86) PCT No.: PCT/JP2012/064250
§ 371 (c)(1),
(2), (4) Date: Nov. 22, 2013

(87) PCT Pub. No.: WO2012/161352
PCT Pub. Date: Nov. 29, 2012

(65) Prior Publication Data
US 2014/0147917 A1 May 29, 2014

(30) Foreign Application Priority Data
May 25, 2011 (JP) ................... 2011-117321

(51) Int. Cl.
| | |
|---|---|
| C12N 15/86 | (2006.01) |
| A61K 48/00 | (2006.01) |
| A61K 38/00 | (2006.01) |
| C07K 14/47 | (2006.01) |
| A61K 38/17 | (2006.01) |
| A61K 35/761 | (2015.01) |

(52) U.S. Cl.
CPC .............. *C12N 15/86* (2013.01); *A61K 35/761* (2013.01); *A61K 38/1709* (2013.01); *C07K 14/4702* (2013.01); *A61K 48/0066* (2013.01); *C12N 2710/10332* (2013.01); *C12N 2710/10343* (2013.01); *C12N 2830/15* (2013.01); *C12N 2830/30* (2013.01)

(58) Field of Classification Search
None
See application file for complete search history.

(56) References Cited

U.S. PATENT DOCUMENTS

| | | | |
|---|---|---|---|
| 5,168,062 A | 12/1992 | Stinski | |
| 5,385,839 A | 1/1995 | Stinski | |
| 5,489,527 A | 2/1996 | Wilson | |
| 2004/0148647 A1 | 7/2004 | Enenkel et al. | |
| 2006/0275263 A1 | 12/2006 | Namba et al. | |
| 2009/0005538 A1* | 1/2009 | Kumon et al. ................ | 530/350 |
| 2010/0160415 A1 | 6/2010 | Solvason et al. | |
| 2011/0269824 A1 | 11/2011 | Kumon et al. | |
| 2012/0309050 A1* | 12/2012 | Kumon et al. ................ | 435/69.1 |

FOREIGN PATENT DOCUMENTS

| | | |
|---|---|---|
| CN | 101993892 A | 3/2011 |
| JP | 2814433 B2 | 8/1998 |
| JP | 2814434 B2 | 10/1998 |
| JP | 2006-507829 A | 3/2006 |
| JP | 2009-511014 A | 3/2009 |
| JP | 2009-114103 A | 5/2009 |
| WO | WO 01/38528 A1 | 5/2001 |
| WO | WO 2007/070392 A2 | 6/2007 |
| WO | WO 2008/091276 A2 | 7/2008 |
| WO | WO 2011/062298 A1 | 5/2011 |
| WO | WO 2012/002582 A1 | 1/2012 |

OTHER PUBLICATIONS

Sequence Alignment SEQ ID No. 1 with SEQ ID No. 1 of U.S. Patent Application Publication No. 2009/0005538. STIC Sequence Search Conducted on Aug. 29, 2014. 2 pages.*
Abarzua et al., "An N-terminal 78 amino acid truncation of REIC/Dkk-3 effectively induces apoptosis," Biochemical and Biophysical Research Communications, 2008, 375(4):614-618.
Kim et al., "Preferentially enhanced gene expression from a synthetic human telomerase reverse transcriptase promoter in human cancer cells," Oncology Reports, 2006, 16:975-979.
Watanabe, Masami, "Next-Generation Gene/Protein Therapy Led by Ultrahigh-Efficiency Gene Expression System," The Japanese Journal of Urology, Mar. 2011, 102(2):218, frontier 8-3, with English translation.
Office Action dated Jul. 22, 2014, in CN 201280025035.X, 7 pages.
European Search Report dated Jan. 21, 2015, in EP 12789513.4, 5 pages.
Edamura et al., "Adenovirus-mediated REIC/Dkk-3 gene transfer inhibits tumor growth and metastasis in an orthotopic prostate cancer model," Cancer Gene Therapy, Jun. 29, 2007, 14(9):765-772.
Kawasaki et al., "REIC/Dkk-3 overexpression downregulates P-glycoprotein in multidrug-resistant MCF7/ADR cells and induces apoptosis in breast cancer," Cancer Gene Therapy, 2009, published online Jul. 25, 2008, 16(1):65-72.
Sakaguchi et al., "Overexpression of REIC/Dkk 3 in Normal Fibroblasts Suppresses Tumor Growth via Induction of Interleukin-7," Journal of Biological Chemistry, Mar. 11, 2009, 284(21):14236-14244.
Watanabe et al., "A novel gene expression system strongly enhances the anticancer effects of a REIC/Dkk-3-encoding adenoviral vector," Oncology Reports, 2014, available online Dec. 31, 2013, 31:1089-1095.

* cited by examiner

*Primary Examiner* — Catherine S. Hibbert
*Assistant Examiner* — Channing S Mahatan
(74) *Attorney, Agent, or Firm* — Foley & Lardner LLP

(57) ABSTRACT

An objective of the present invention is to provide an adenovirus vector expressing a REIC/Dkk-3 protein at a high level and containing a DNA construct for expression of REIC/Dkk-3 DNA, wherein the DNA construct is prepared by ligating, from the 5' terminal side,
 (i) a CMV promoter,
 (ii) REIC/Dkk-3 DNA,
 (iii) a polyA addition sequence, and
 (iv) enhancers prepared by linking an hTERT (Telomerase Reverse Transcriptase) enhancer, an SV40 enhancer, and a CMV enhancer in this order.

8 Claims, 11 Drawing Sheets

Fig. 2 pshuttle- REIC-TSC

```
     (1)           (2)
XbaI-REIC-KpnI-3xenh-EcoRI
```

T/CTAGAGCaccatgcagcggcttggggccaccctgctgtgcctgctgctggcggcggcggt (1)
ccccacggccccgcgcccgctccgacggcgacctcggctccagtcaagcccggcccggctc
tcagctacccgcaggaggaggccaccctcaatgagatgttccgcgaggttgaggaactgatg
gaggacacgcagcacaaattgcgcagcgcggtggaagagatggaggcagaagaagctgctgc
taaagcatcatcagaagtgaacctggcaaacttacctcccagctatcacaatgagaccaaca
cagacacgaaggttggaaataataccatccatgtgcaccgagaaattcacaagataaccaac
aaccagactggacaaatggtcttttcagagacagttatcacatctgtgggagacgaagaagg
cagaaggagccacgagtgcatcatcgacgaggactgtgggcccagcatgtactgccagtttg
ccagcttccagtacacctgccagccatgccggggccagaggatgctctgcacccgggacagt
gagtgctgtggagaccagctgtgtgtctggggtcactgcaccaaaatggccaccaggggcag
caatgggaccatctgtgacaaccagagggactgccagccggggctgtgctgtgccttccaga
gaggcctgctgttcctgtgtgcacacccctgcccgtggagggcgagcttttgccatgacccc
gccagccggcttctggacctcatcacctgggagctagagcctgatggagccttggaccgatg
cccttgtgccagtggcctcctctgccagccccacagccacagcctggtgtatgtgtgcaagc
cgaccttcgtggggagccgtgaccaagatggggagatcctgctgcccagagaggtccccgat
gagtatgaagttggcagcttcatggaggaggtgcgccaggagctggaggacctggagaggag
cctgactgaagagatggcgctggggagcctgcggctgccgccgctgcactgctgggaggggg
aagagatttagGGGGTAC/CCCGGCtagatgactaacGTTTAAACCCGCTGATCAGCCTCGA
CTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATTGGGAAG
ACAATAGCAGGCATGCTGGGGATGCGGTGGGCTCTATGGcggagtactgtcctccgcttccc (2)
acgtggcggagggactggggacccgggcacccgtcctgccccttcaccttccagctccgcct
cctccgcgcggaccccgcccgtcccgacccctcccgggtcccggccccagccccctccggg
ccctcccagccctcccttcctttccgcggccccgccctctcctcgcggcgcgagtttTGG
AAAGTCCCCAGGCTCCCCAGCAGGCAGAAGTATCCAAAGCATCCATCTCAATTAGTCAGCAA
CCAGGTGTGGAAAGTCCCCAGGCTCCCCAGCAGGCAGAAGTATCCAAAGCATCCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTATTTATGCAGAGGCCGAGGCCGCCT
CTGCCTCTGAGCTATTCCAGAAGTAGTGAGGAGGCTTTTTTGGAGGCCAAGGCTTTTGCAAA
AAGCTCcgttacataacttacggtaaatggcccgcctggctgaccgcccaacgaccccgcc
cattgacgtcaataatgacgtatgttcccatagtaacgccaataggactttccattgacgt
caatgggtggagtatttacggtaaactgcccacttggcagtacatcaagtgtatcatatgcc
aagtacgccccctattgacgtcaatgacggtaaatggcccgcctggcattatgcccagtaca
tgaccttatgggactttcctacttggcagtacatctacgtattagtcatcgctattaccatg
gtgatgcggttttggcagtacatcaatgggcgtggatagcggtttgactcacggggatttcc
aagtctccaccccattgacgtcaatgggagtttgttttggcaccaaaatcaacgggactttc
caaaatgtcgtaacaactccgccccattgacgcaaatgggcggtaggcgtgTTGCCGG/AAT
TC Lane M: size marker(DNA Marker DL2000: from the top 2000, 1000, 750, 500, 250, 100bp)
Lane 1- 8: Clone #1-8

Lane M1: λ-Hind III Digest
Lane M2: size marker(DNA Marker DL2000: from the top 2000, 1000, 750, 500, 250, 100bp)
Lane M3: Wide Range DNA Marker(500-12,000)
Lane1: Adeno-X-REIC-TSC plasmid(500 ng apply)
Lane2: XhoI-digested DNA Adeno-X-REIC-TSC plasmid
Lane3: PacI-digested DNA Adeno-X-REIC-TSC plasmid Lane M: size marker(TaKara Code 3415A)
Lane 1: XhoI-digested Adeno-X-hREIC Lane M: size marker Wide Range DNA Ladder
Lane N: Negative control(HeLa cell)
Lane N': Negative control(no template)
Lane P: Positive control
Lane 1: Adeno-X-hREIC Bar = 1 cm

REIC-EXPRESSING ADENOVIRUS VECTOR

CROSS-REFERENCE TO RELATED APPLICATIONS

This application is a national phase of international application PCT/JP2012/064250, filed May 25, 2012, which was published on Nov. 29, 2012, as WO 2012/161352, which claims the benefit of Japanese application No. 2011-117321, filed May 25, 2011. Each of these applications is incorporated herein by reference in its entirety.

TECHNICAL FIELD

The present invention relates to an adenovirus vector containing a promoter, an enhancer, and the like and expressing the REIC/Dkk-3 protein at a high level.

BACKGROUND ART

Various gene expression promoters such as CMV and CAG promoters have been developed to increase gene expression efficiency (Patent Documents 1-4). However, in the field of biotechnology, even when these conventional techniques are used, problems regularly occur, such that almost no gene expression takes place or the amount of the thus expressed protein is extremely low, depending on cell types or gene types. These problems cause big barriers to the development of medical care using gene expression for diagnosis or treatment.

Meanwhile, the REIC/Dkk-3 gene is known to be a gene relating to cell immortalization. It has been reported that the expression of this gene is suppressed in cancer cells. It has also been reported that the REIC/Dkk-3 gene has been used for cancer therapy (Patent Document 5).

CITATION LIST

Patent Documents

Patent Document 1 JP Patent Publication No. 2814433
Patent Document 2 JP Patent Publication No. 2814434
Patent Document 3 U.S. Pat. No. 5,168,062 Description
Patent Document 4 U.S. Pat. No. 5,385,839 Description
Patent Document 5 International Patent Publication WO01/038523 pamphlet

SUMMARY OF THE INVENTION

An objective of the present invention is to provide an adenovirus vector expressing high levels of the REIC/Dkk-3 protein.

The present inventors have examined the use of the REIC/Dkk-3 gene for gene therapy against cancer and have found that the incorporation of the REIC/Dkk-3 gene into an expression vector that is administered to a living body exhibits an effect in cancer therapy. The present inventors have intensively examined a method to cause the expression of the REIC/Dkk-3 gene at a higher level in vivo, considering the possibility that in vivo expression of the REIC/Dkk-3 gene at such a high level could increase therapeutic effects against cancer.

The present inventors have attempted the development of a new gene expression system using a promoter, which enables gene expression with higher efficiency. Specifically, promoter activity has been compared and examined using combinations of various gene promoters and enhancers.

As a result, they have discovered that the REIC/Dkk-3 gene is expressed at a significantly high level in vivo and exhibits significantly improved therapeutic effects against cancer when a CMV (cytomegalovirus) promoter was used as a prompter and a construct prepared by ligating REIC/Dkk-3 DNA to a site downstream of a CMV (cytomegalovirus) promoter, ligating a polyA sequence to a site downstream of the DNA, and ligating enhancers prepared by linking an hTERT (Telomerase Reverse Transcriptase) enhancer, an SV40 enhancer, and a CMV enhancer in this order to a site downstream of the polyA sequence is inserted into an adenovirus vector, which is then administered to a living body. They thus have completed the present invention. Specifically, the present invention is as described below.

[1] A DNA construct for the expression of REIC/Dkk-3 DNA, which is prepared by ligating, from the 5' terminal side:
  (i) a CMV promoter;
  (ii) the following REIC/Dkk-3 DNA:
    (a) DNA comprising the nucleotide sequence shown in SEQ ID NO: 1,
    (b) DNA hybridizing under stringent conditions to DNA comprising a nucleotide sequence complementary to the nucleotide sequence shown in SEQ ID NO: 1 and encoding a protein having cancer cell death-inducing activity and/or tumor cell growth-suppressing activity,
    (c) a polynucleotide comprising a nucleotide sequence ranging from the $1^{st}$ nucleotide to any single nucleotide from the $117^{th}$ nucleotide to the $234^{th}$ nucleotide in the nucleotide sequence shown in SEQ ID NO: 1, or
    (d) a polynucleotide hybridizing under stringent conditions to a polynucleotide that comprises a nucleotide sequence complementary to a nucleotide sequence ranging from the $1^{st}$ nucleotide to any single nucleotide from the $117^{th}$ nucleotide to the $234^{th}$ nucleotide in the nucleotide sequence shown in SEQ ID NO: 1, and encoding a polypeptide having cancer cell death-inducing activity and/or tumor cell growth suppressing activity;
  (iii) a polyA addition sequence; and
  (iv) enhancers prepared by linking an hTERT (Telomerase Reverse Transcriptase) enhancer, an SV40 enhancer, and a CMV enhancer in this order.
[2] The DNA construct of [1], wherein the polyA addition sequence is a polyA addition sequence (BGA polyA) derived from a bovine growth hormone gene.
[3] The DNA construct of [1] or [2], containing the nucleotide sequence shown in SEQ ID NO: 6, wherein (ii) REIC/Dkk-3 DNA, (iii) the polyA addition sequence, and (iv) enhancers prepared by linking the hTERT (Telomerase Reverse Transcriptase) enhancer, the SV40 enhancer, and the CMV enhancer in this order, are ligated.
[4] An adenovirus vector, containing the DNA construct of [1] or [2].
[5] A cancer cell death-inducing agent, containing the adenovirus vector of [4].
[6] A tumor cell growth-suppressing agent, containing the adenovirus vector of [4].
[7] A cancer therapeutic drug, containing the adenovirus vector of [4].

The adenovirus vector contains a DNA construct for expression of REIC/Dkk-3 DNA, wherein the DNA construct is prepared by ligating, from the 5' terminal side, (i) a CMV promoter; (ii) REIC/Dkk-3 DNA, (iii) a polyA addition sequence, and (iv) enhancers prepared by linking an hTERT (Telomerase Reverse Transcriptase) enhancer, an SV40 enhancer, and a CMV enhancer in this order. The adenovirus vector can: express REIC/Dkk-3 DNA at a high level in vivo; exhibit a higher gene expression level than an adenovirus vector containing a DNA construct that is prepared by ligating REIC/Dkk-3 DNA to a site downstream of a CMV promoter or a CAG promoter, but lacks the above enhancers; induce cancer-selective cell death; and suppress tumor growth. Therefore, the adenovirus vector of the present invention can be favorably used for gene therapy against cancer using REIC/Dkk-3 DNA.

This description includes part or all of the contents as disclosed in the description and/or drawings of Japanese Patent Application No. 2011-117321, which is a priority document of the present application.

BRIEF DESCRIPTION OF THE DRAWINGS

FIG. 2 shows the nucleotide sequence of the REIC/Dkk-3 DNA expression construct of the present invention.

EMBODIMENTS FOR CARRYING OUT THE INVENTION

Hereafter, the present invention is described in detail.

Figure 1:
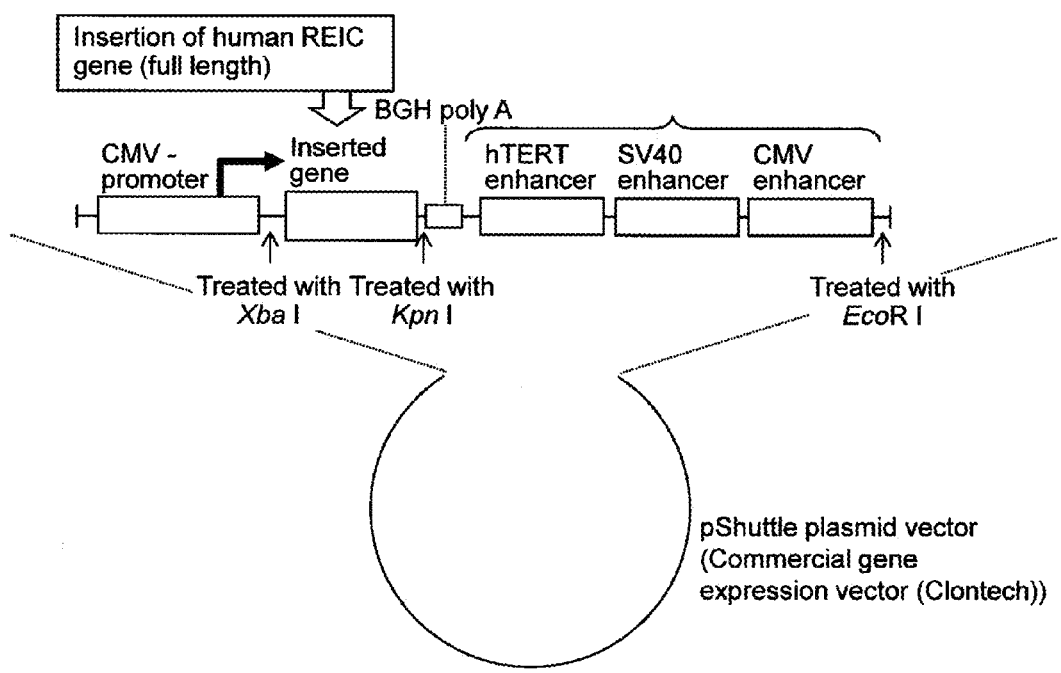
FIG. 1 shows the structure of the REIC/Dkk-3 DNA expression construct of the present invention.

The present invention relates to a DNA construct containing REIC/Dkk-3 DNA, which can be used for REIC protein expression, and further relates to a recombinant adenovirus vector containing the DNA construct. The structure of the DNA construct of the present invention is shown in FIG. 1.

The nucleotide sequence of REIC/Dkk-3 DNA is shown in SEQ ID NO: 1. Furthermore, the amino acid sequence of the REIC/Dkk-3 protein that is encoded by REIC/Dkk-3 DNA is shown in SEQ ID NO: 2. In the present invention, REIC/Dkk-3 may also be referred to as "REIC."

Moreover, the DNA of REIC/Dkk-3 contained in the DNA construct of the present invention is:

DNA hybridizing under stringent conditions to DNA having a nucleotide sequence complementary to the nucleotide sequence shown in SEQ ID NO: 1;

DNA having at least 85%, preferably at least 90%, further preferably at least 95%, and particularly preferably at least 97% sequence identity with the nucleotide sequence shown in SEQ ID NO: 1, when calculated using BLAST (Basic Local Alignment Search Tool) at the National Center for Biological Information (NCBI) or the like (with the use of, for example, default (i.e., initial) parameters); or DNA encoding a protein that comprises an amino acid sequence having a substitution, a deletion and/or an addition of one or a plurality of or several (1 to 10, preferably 1 to 5, and further preferably 1 or 2) amino acids with respect to the amino acid sequence of the protein encoded by the above DNA; which encodes a protein having cancer cell death-inducing activity and/or tumor cell growth-suppressing activity.

Under "stringent conditions" referred to herein, for example, hybridization is carried out with about 1×SSC, 0.1% SDS, and 37° C. Under more stringent conditions, it is carried out with about 0.5×SSC, 0.1% SDS, and 42° C. Under further stringent conditions, it is carried out with about 0.2×SSC, 0.1% SDS, and 65° C. With the higher stringency of hybridization conditions, the isolation of DNA having higher homology with a probe sequence can be expected. However, the above combinations of SSC, SDS and temperature conditions are given only for illustrative purposes. Through appropriate combination of probe concentration, probe length, hybridization reaction time, and the like, required stringency can be realized. Persons skilled in the art can adequately determine such "stringent conditions" as conditions where DNA with high sequence identity can hybridize. Furthermore, the DNA of REIC/Dkk-3 contained in the DNA construct of the present invention is DNA encoding the protein shown in SEQ ID NO: 2.

Moreover, REIC/Dkk-3 DNA contained in the DNA construct of the present invention is a fragmental nucleotide comprising a partial nucleotide sequence of the nucleotide sequence of the DNA, including nucleotides which encode a peptide having cancer cell death-inducing activity and/or tumor cell growth-suppressing activity. Such a fragmental nucleotide can be easily obtained by cleaving the full-length REIC/Dkk-3 DNA at appropriate sites and then determining whether the resultant has cancer cell death-inducing activity and/or tumor cell growth-suppressing activity. Examples of such a fragmental nucleotide include: a polynucleotide comprising a nucleotide sequence ranging from the $1^{st}$ nucleotide to any single nucleotide from the $117^{th}$ to the $234^{th}$ nucleotides in the nucleotide sequence of REIC/Dkk-3 DNA shown in SEQ ID NO: 1; and a polynucleotide hybridizing under stringent conditions to a polynucleotide comprising a nucleotide sequence complementary to the nucleotide sequence ranging from the $1^{st}$ nucleotide to any single nucleotide from the $117^{th}$ to the $234^{th}$ nucleotides in the nucleotide sequence of REIC/Dkk-3 DNA shown in SEQ ID NO: 1; each of which encodes a polypeptide having cancer cell death-inducing activity and/or tumor cell growth-suppressing activity. Examples of such a polynucleotide comprising a nucleotide sequence ranging from the $1^{st}$ nucleotide to any single nucleotide from the $117^{th}$ to the $234^{th}$ nucleotides in the nucleotide sequence of REIC/Dkk-3 DNA shown in SEQ ID NO: 1 include the polynucleotide (SEQ ID NO: 3) ranging from the $1^{st}$ to the $117^{th}$ nucleotides and the polynucleotide (SEQ ID NO: 4) ranging from the $1^{st}$ to the $234^{th}$ nucleotides. Polypeptides encoded by these polynucleotides having cancer cell death-inducing activity and/or tumor cell growth-suppressing activity are described in U.S. patent application publication No. 2011-0269824, which corresponds to JP Patent Publication (Kokai) No. 2009-114103 A, for example.

REIC/Dkk-3 DNA can be obtained from human cells, human tissue, and the like based on the sequence information of SEQ ID NO: 1. REIC/Dkk-3 DNA can also be obtained according to WO01/038523.

The DNA construct is prepared by ligating a CMV (cytomegarovirus) promoter to a site upstream of REIC/Dkk-3 DNA, and a polyA addition sequence (polyadenylation sequence, polyA) to a site downstream of REIC/Dkk-3 DNA. Examples of the origin of the polyA addition sequence (polyadenylation sequence, polyA) include, but are not limited to, a growth hormone gene-derived polyA addition sequence (e.g., a bovine growth hormone gene-derived polyA addition sequence (BGA polyA)) (contained in the nucleotide sequence shown in SEQ ID NO: 5 (the sequence of the 13$^{th}$ nucleotide and nucleotides following thereto)), a human growth hormone gene-derived polyA addition sequence, an SV40 virus-derived polyA addition sequence, and a human or rabbit globin gene-derived polyA addition sequence. Transcriptional efficiency is increased by causing the DNA construct to contain such a polyA addition sequence. Moreover, enhancers (3×enh) prepared by linking an hTERT (Telomerase Reverse Transcriptase) enhancer, an SV40 enhancer, and a CMV (cytomegarovirus) enhancer in this order are ligated to a site downstream of the polyA addition sequence (in FIG. 2, the "3×enh" portion denotes the relevant sequence; and the sequence in FIG. 2 is shown in SEQ ID NO: 6). Specifically, the DNA construct is prepared by ligating, from the 5' terminal side, (i) a CMV promoter, (ii) REIC/Dkk-3 DNA, (iii) a polyA addition sequence, and (iv) enhancers prepared by linking the hTER (Telomerase Reverse Transcriptase) enhancer, the SV40 enhancer, and the CMV enhancer in this order.

The above elements should be functionally linked (ligated) to each other. The expression used herein, "functionally linked (ligated) to each other" means that elements are linked or ligated to each other so that each element can exhibit its functions so as to enhance the expression of a gene to be expressed.

The above expression cassette can be obtained by inserting REIC/Dkk-3 DNA into a pShuttle vector (Clonetech) containing a foreign gene insertion site downstream of a commercial CMV promoter, and a BGA polyA sequence downstream of the insertion site, and then ligating an hTERT (Telomerase Reverse Transcriptase) enhancer, an SV40 enhancer, and a CMV enhancer in this order to a site downstream of the BGA polyA sequence.

The structure of a portion of the DNA construct containing REIC/Dkk-3 DNA of the present invention, which lacks the CMV promoter, is shown in FIG. 2, and the sequence thereof is shown in SEQ ID NO: 6. In FIG. 2, a BGA polyA sequence is contained between REIC/Dkk-3 DNA and 3×enh. The DNA construct containing REIC/Dkk-3 DNA of the present invention has a CMV promoter upstream (5' side) of the sequence shown in SEQ ID NO: 4.

The DNA construct of the present invention is used after introduction thereof into an adenovirus vector. The present invention also encompasses an adenovirus vector containing the DNA construct for expression of REIC/Dkk-3 DNA. A vector system containing the DNA construct of the present invention is referred as an SGE (Super Gene Expression) system. For example, an adenovirus vector containing a DNA construct that contains REIC/Dkk-3 DNA and a CMV promoter is referred to as Ad-SGE-CMV-REIC. The above adenovirus vector containing the DNA construct is obtained by preparing a recombinant adenovirus through introduction of the DNA construct into an adenovirus vector. Introduction of the DNA construct into an adenovirus can be performed by introducing the DNA construct in a pShuttle vector containing the DNA construct of the present invention into an adenovirus, for example.

An adenovirus vector is characterized in that: (1) it enables gene transfer into many types of cells; (2) it enables efficient gene transfer into even cells at the stationary phase; (3) it can be concentrated by centrifugation, and thus a high-titer virus (10-11 PFU/ml or more) can be obtained; (4) and it is suitable for direct gene transfer into in vivo tissue cells.

As adenoviruses for gene therapy, the first generation adenovirus vector prepared by deleting the E1/E3 region (Miyake, S., et al., Proc. Natl. Acad. Sci. U.S.A., 93, 1320, 1996), the second generation adenovirus vector prepared by deleting, in addition to the E1/E3 region, the E2 or E4 region (Lieber, A., et al., J. Virol., 70, 8944, 1996; Mizuguchi, H. & Kay, M. A., Hum. Gene Ther., 10, 2013, 1999), and the third generation adenovirus vector prepared by almost completely deleting the adenovirus genome (GUTLESS) (Steinwaerder, D. S., et al., J. Virol., 73, 9303, 1999) have been developed. Any of these adenovirus vectors can be used without particular limitation for the gene transfer according to the present invention.

A recombinant adenovirus vector containing the DNA construct that contains REIC/Dkk-3 DNA of the present invention is administered to a human subject or a subject that is another mammal, so that a gene for cancer therapy is delivered to cancer cells of the subject, the gene is expressed in cancer cells, cell death is induced selectively for cancer cells, and/or tumor cell growth is suppressed so that therapeutic effects are exhibited against cancer. The present invention encompasses a viral preparation for cancer therapy containing such an adenovirus vector. Examples of cancer to be treated herein include, but are not limited to, brain/nerve tumor, skin cancer, gastric cancer, lung cancer, hepatic cancer, lymphoma/leukemia, colon cancer, pancreatic cancer, anal/rectal cancer, esophageal cancer, uterine cancer, breast cancer, adrenal cancer, kidney cancer, renal pelvic and ureteral cancer, bladder cancer, prostate cancer, urethral cancer, penile cancer, testicular cancer, osteoma/osteosarcoma, leiomyoma, rhabdomyoma, and mesoepithelioma. The adenovirus vector of the present invention can also be used for treatment of primary cancer and metastatic cancer. Furthermore, the present invention further encompasses a method for treating cancer by administering the above adenovirus vector to a subject.

The adenovirus vector of the present invention can be administered by methods that can be used in the field of gene therapy, such as via intravascular administration (e.g., intravenous administration and intraarterial administration), peroral administration, intraperitoneal administration, intratracheal administration, intrabronchial administration, subcutaneous administration, or transdermal administration. In particular, the adenovirus vector of the present invention has strong directivity toward a specific tissue or cells, and thus is capable of efficiently delivering a target gene to a specific tissue or cells. Therefore, efficient diagnosis and treatment can be performed even through intravascular administration of the adenovirus vector.

The adenovirus vector may be administered at a therapeutically effective dose, which can be easily determined by persons skilled in the field of gene therapy. Furthermore, the dose can be adequately varied depending on the severity of the pathological condition, gender, age, body weight, lifestyle, and the like of the subject. For example, the adenovirus vector may be administered in doses ranging from $0.5 \times 10^{11}$ to $2.0 \times 10^{12}$ viral genome/kg body weight, preferably ranging from $1.0 \times 10^{11}$ to $1.0 \times 10^{12}$ viral genome/kg body weight, and further preferably ranging from $1.0 \times 10^{11}$ to $5.0 \times 10^{11}$ viral genome/kg body weight. The term "viral genome" represents the number of molecules of the genome of an adenovirus (viral particle count), and is also referred as "particle(s)." The adenovirus vector contains a carrier, a diluent, and an excipient which are generally used in the field of formulation. For example, lactose, magnesium stearate, and the like are used as carriers or excipients for tablets. An aqueous solution is used for injection, such as physiological saline or an isotonic solution containing dextrose or another adjuvant, and this can be used in combination with an appropriate solubilizing agent (e.g., alcohol, polyalcohol such as propylene glycol, and nonionic surfactant). As an oily fluid, sesame oil, soybean oil, or the like is used. As a solubilizing agent, benzyl benzoate, benzyl alcohol, or the like can also be used in combination therewith.

The present invention is hereafter described in detail with reference to the following examples, although the present invention is not limited thereto.

Example 1

Construction of a pShuttle-REIC-TSC Plasmid

The DNA construct of the present invention containing a human REIC/Dkk-3 gene as a foreign gene (i.e., a gene to be inserted) was prepared. The DNA construct (FIG. 1) used herein was constructed by inserting DNA encoding the REIC/Dkk-3 protein into the insertion site of Xba 1-Kpn 1 of a commercial pShuttle plasmid vector (Clontech), and further inserting three enhancers (an hTERT enhancer, an SV40 enhancer, and a CMV enhancer; such enhancers are hereinafter referred to as "TSC") into the insertion site of Kpn 1-EcoR 1 downstream of the DNA encoding the REIC/Dkk-3 protein to form BGH poly A+3 enhancers. FIG. 2 shows the nucleotide sequence [SEQ ID NO: 6] of a construct in which DNA encoding REIC was inserted (excluding the CMV promoter sequence). SEQ ID NO: 7 shows the nucleotide sequence of the region containing BGH poly A and three enhancers (contained in the above construct). In FIG. 2, portions (1) and (2) enclosed by frames in the nucleotide sequence indicate DNA encoding the REIC/Dkk-3 protein and the three enhancers (3×enh), respectively. The pShuttle plasmid vector containing the above construct is referred to as a "pShuttle-REIC-TSC plasmid."

Example 2

Preparation of Ad-SGE-CMV-REIC

A recombinant adenovirus vector containing the above construct was further constructed.

For construction, an Adeno-X (trademark) Expression System 1 (TaKaRa Code.Z1513N) and a Plasmid Midi kit (QIAGEN Code.12143) were used.

The recombinant adenovirus vector containing the construct shown in FIG. 1 is referred to as "Ad-SGE-CMV-REIC."

1. Construction of Adeno-X Plasmid

Figure 3:
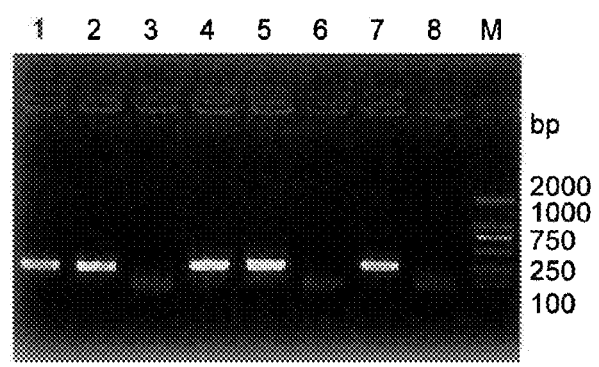
FIG. 3 shows the results of confirming inserts in the constructed adenovirus vector containing the construct of the present invention.

The pShuttle-REIC-TSC plasmid was digested with restriction enzymes, PI-Sce I, I-Ceu I, and thus an expression cassette specific to the target gene was obtained. The expression cassette was ligated to Adeno-X Viral DNA, and then the ligation product was digested with Swa I. Electro competent cells, DH10B, were transformed with the ligation product, and then the cells were plated on an LB agar medium supplemented with ampicillin. The thus obtained colonies were picked up and then amplified with an Adeno-X System PCR Screening Primer Set. Amplification bands were confirmed by electrophoresis. A 287-bp amplification band was obtained for the Adeno-X plasmid DNA containing the target gene expression cassette, and thus the selected colonies #1, 2, 4, 5, and 7 were confirmed to be target plasmids (FIG. 3). Sequencing was performed for the selected colony #4 using primers constructed upstream and downstream of the cloning site Swa I. The analytical results confirmed that the target gene had been inserted forward in the recombinant plasmid, and that the ligation had caused no excessive insertion or deletion of nucleotides.

Figure 4:
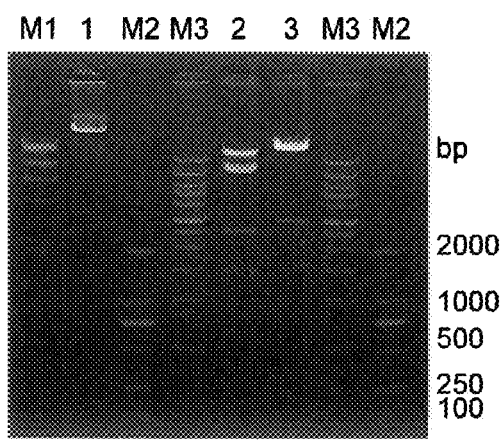
FIG. 4 shows the results of confirming the structure of the constructed adenovirus vector containing the construct of the present invention.

*Escherichia coli* was transformed with the selected clone #4, and then cultured with shaking in an LB medium containing ampicillin. On the next day, plasmid DNA was purified from the cultured cells using a DNA purification kit. The resultant was partially digested with restriction enzymes Xho I, Pac I, and then electrophoretic bands indicating expected fragment sizes were detected by agarose gel electrophoresis (digested with Xho I: 0.6 kbp, 1.4 kbp, 2.6 kbp, 8 kbp, 9 kbp, and 14.5 kbp; and digested with Pac I: 2.9 kbp and 33.3 kbp in FIG. 4)

It was thus confirmed that clones obtained by scale-up preparation were target recombinant plasmids.

2. Preparation of Recombinant Adenovirus (i) Preparation of Primary Virus 293 cells were cultured in DMEM containing 10% FBS, 2 mML (final concentration)-glutamine and a 1% penicillin-streptomycin solution in a 6-cm collagen coated Petri dish to 100% confluency. AdenoX-REIC-TSC plasmid (5 µg) digested with Pac I restriction enzyme was transfected using TransIT-293. 24 hours later, medium exchange was performed. After confirmation of cell degradation on day 13, cells were collected. A cell pellet was suspended uniformly in medium, freezing and thawing were repeated 3 times, and then the supernatant obtained by centrifugation was determined to be each primary viral solution.

(ii) Preparation of Secondary Virus 293 cells that had been cultured in the 6-cm collagen coated Petri dish to 70% to 100% confluency were infected with the primary viral solution. Upon viral infection, DMEM containing 5% FBS, 2 mML (final concentration)-glutamine, and a 1% penicillin-streptomycin solution was used. After confirmation of the degradation of the 293 cells, cells were collected, freezing and thawing were repeated 3 times, and then the supernatant obtained by centrifugation was determined to be a secondary virus.

(iii) Preparation of Tertiary Virus 293 cells that had been cultured in a T-75 collagen coated flask to 70% to 100% confluency were infected with the secondary virus. After confirmation of the complete degradation of the 293 cells, the culture solution containing the cells was recovered. After ultrasonication, the supernatant obtained by centrifugation was determined to be a tertiary virus. The resultant was aliquoted at 1 mL/vial, rapidly frozen with dry ice, and then stored at −80° C.

3. Method for Preparation of Purified Recombinant Adenovirus (i) Scale-Up Preparation 293 cells were cultured in a multilayer cell culture flask until confluent. The tertiary virus titer was confirmed using an Adeno-X (trademark)-Rapid Titer Kit, and then the 293 cells were infected therewith under optimum conditions. After confirmation of the complete degradation of the 293 cells, the cells were collected, and then subjected to freezing and thawing. The supernatant obtained by centrifugation of the resultant was determined to be a viral solution.

(ii) Purification by Cesium Chloride Density-Gradient Centrifugation Method

A cesium chloride solution and the viral solution obtained in (i) above were layered using an ultracentrifugation tube, and then the resultant was subjected to centrifugation at 4° C. and 25,000 rpm for 2 hours. The virus bands formed were collected. A cesium chloride solution was further added, ultracentrifugal separation was performed at 4° C. and 35,000 rpm for 3 hours, and then the virus bands formed were collected. The viral solution was collected by performing ultracentrifugation twice and then dialyzed against 10% glycerol-containing PBS(−) using a dialysis cassette. The solution collected by dialysis was aliquoted (0.5 mL each), and then cryopreserved at −80° C.

4. Quality Inspection of Purified Recombinant Adenovirus
(i) Titer Measurement ($TCID_{50}$ Method)

The purified viral solution was diluted $1\times10^6$-fold with medium and subjected to an 11-step serial dilution (three-fold each) on a collagen coated 96-well plate. The 293 cell suspension (50 μl) of the same quantity was added, and then cells were cultured. Control cells were cultured by adding only a 298 cell suspension and medium. On day 14, the end point of cell degradation was determined by observation under a microscope with the naked eye, and then 50% cell degradation end point ($TCID_{50}$) was calculated using the following Kaber formula (Table 1). The $TCID_{50}$ value calculated by this method was well consistent with "pfu", 1 $TCID_{50}$=1 pfu was employed.

$$TCID_{50}=(\text{dilution ratio for the 1}^{st}\text{ line})\times(\text{serial dilution ratio})\Sigma^{-0.5} \quad \text{Kaber formula}$$

Where the sum of (the number of wells with cell degradation)/ (the number of specimens) at Σ=each dilution step

TABLE 1

Results of the measurement of titer

| Virus | Plate # | Titer (pfu/mL) | |
|---|---|---|---|
| Adeno-X-hREIC | 1 | $1.9 \times 10^{10}$ | $2.4 \times 10^{10}$ |
| | 2 | $2.9 \times 10^{10}$ | |

Figure 5:
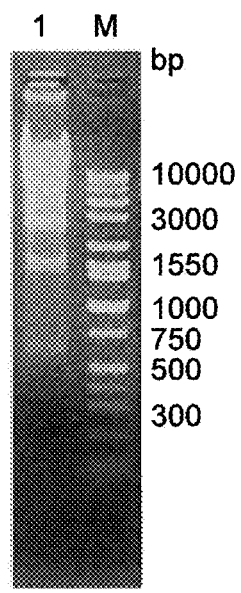
FIG. 5 shows the results of confirming the structure of the purified adenovirus vector containing the construct of the present invention.

(ii) Confirmation of Structure 293 cells that had been cultured on a collagen coated 24-well plate to 70% to 100% confluency were infected with 1 μL of a viral solution prepared by diluting the purified viral solution 10-fold with PBS. After confirmation of complete cell degradation, cells were collected. Total DNA was extracted and prepared, digested with Xho I restriction enzyme, and then subjected to agarose gel electrophoresis. Expected fragment sizes of 0.6 kbp, 1.44 kbp, 2.46 kbp, 6.1 kbp, 8 kbp, and 14.5 kbp were detected. The insertion of DNA fragments of the target size was confirmed (FIG. 5).

(iii) RCA (Replication Competent Adenovirus) Check (PCR Method)

Figure 6:
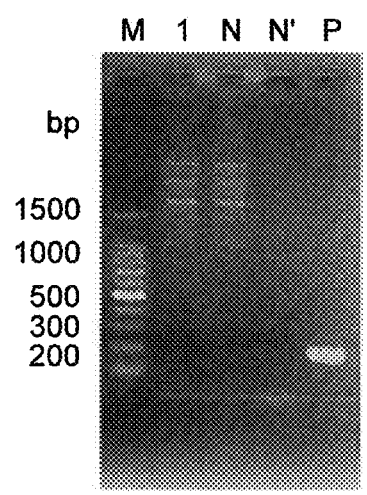
FIG. 6 shows the results of confirmation (check) regarding the RCA (Replication Competent Adenovirus) for the constructed adenovirus vector containing the construct of the present invention.

HeLa cells that had been cultured on a 24-well plate to 70% to 100% confluency were infected with 1 μL of a viral solution prepared by diluting the purified viral solution 10-fold with PBS. Three days later, cells were collected and then used to prepare total DNA. PCR was performed using the extracted DNA as a template and primers for E1A gene detection (sense: 5'-ATGAGACATATTATCTGCCAC-3 (SEQ ID NO: 8) and antisense: 5'-GTAAGTCAATCCCTTCCTGCAC-3') (SEQ ID NO: 9). As a result, the 240-bp E1 gene band to be amplified with the use of these primers was not detected in any of the viral samples, confirming that there was no RCA contamination (FIG. 6).

Example 3

Expression of REIC Protein in Cells Using Ad-SGE-CMV-REIC

PC3 cells or HeLa cells were transfected at 10 MOI (multiplicity of infection) in a serum free medium for 2 hours with:

the recombinant adenovirus vector (Ad-SGE-CMV-REIC) constructed in Example 2; and
a recombinant adenovirus vector (Ad-CMV-REIC) containing a construct that had been prepared by inserting only the CMV promoter to a site upstream of REIC/Dkk-3 DNA (without inserting any 3×enh). After 12 hours, intracellular expression of the human REIC protein was detected by Western blot.

Figure 7:
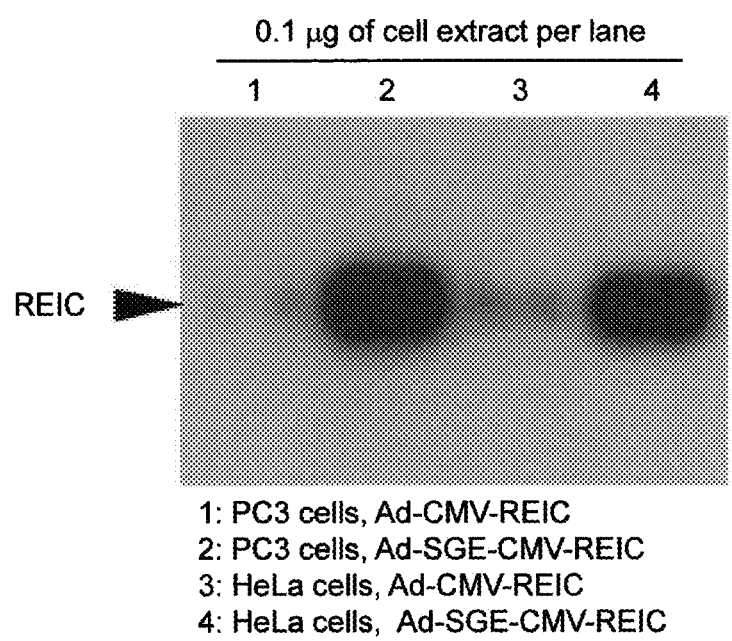
FIG. 7 shows the intensities of REIC-Dkk-3 gene expression when various vectors were used.

The results are shown in FIG. 7. As shown in FIG. 7, REIC gene expression was significantly enhanced when Ad-SGE-CMV-REIC was used, compared to the use of Ad-CMV-REIC.

The results indicate that: increased therapeutic effects (anti-tumor effects) can be expected in human cancer therapy with Ad-SGE-CMV-REIC compared to the use of conventional Ad-CMV-REIC, even when the dosages (viral particles) are the same; and adverse reactions can be expected to be effectively reduced to an extent equivalent to that of the use of conventional Ad-CMV-REIC by further decreasing the dosage of the adenovirus vector.

Example 4

Cell Death Induction by Ad-SGE-CMV-REIC

For examination of in vitro cell death induction, cells were plated on a flat-bottom 6-well plate and then cultured for 24 hours. Cells were transfected with Ad-SGE-CMV-REIC, Ad-CMV-REIC, and a recombinant adenovirus vector (Ad-CAG-REIC) containing a construct prepared by inserting only a CAG promoter (the CAG promoter having a structure prepared by ligating a CMV enhancer and a chicken β-actin promoter to a site upstream of REIC/Dkk-3 DNA) without inserting any 3×enh, at 50 MOI (multiplicity of infection) in serum free media for 2 hours, followed by medium exchange with fresh complete media. An adenovirus vector (Ad-LacZ) containing a LacZ gene was used a control. After 48 hours of incubation, a Hoechst33342 stock solution with a concentration of 2 μg/ml was added, and then cells were incubated in dark conditions for 10 minutes. Hoecht33342 is an interchelator dye that can be used when examining the total amount and degree of the condensation of chromatin (Belloc F et al., Cytometry 1994; 17: 59-65, Maciorowski Z et al., Cytometry 1998; 32: 44-50). Cells with highly condensed and segmented nuclei observed using a fluorescent microscope were identified as non-viable (cell death), and then counted in 3 to 5 different visual fields under a microscope.

To detect cells, for which cell death had been confirmed in vivo, a TUNEL (terminal deoxynucleotidyl transferase-mediated UTP end labeling) assay was performed using an In situ Cell Detection Kit (Fluorescein (Roche)). Specifically, tumor tissue was cut, immersed in an OCT compound, and then quickly frozen in liquid nitrogen. Frozen section (10 μm) samples were fixed and washed using methanol for 30 minutes at room temperature, impregnated with PBS containing 0.1% Triton X-100, and then stained with a TUNEL reaction mixture.

Figure 8:
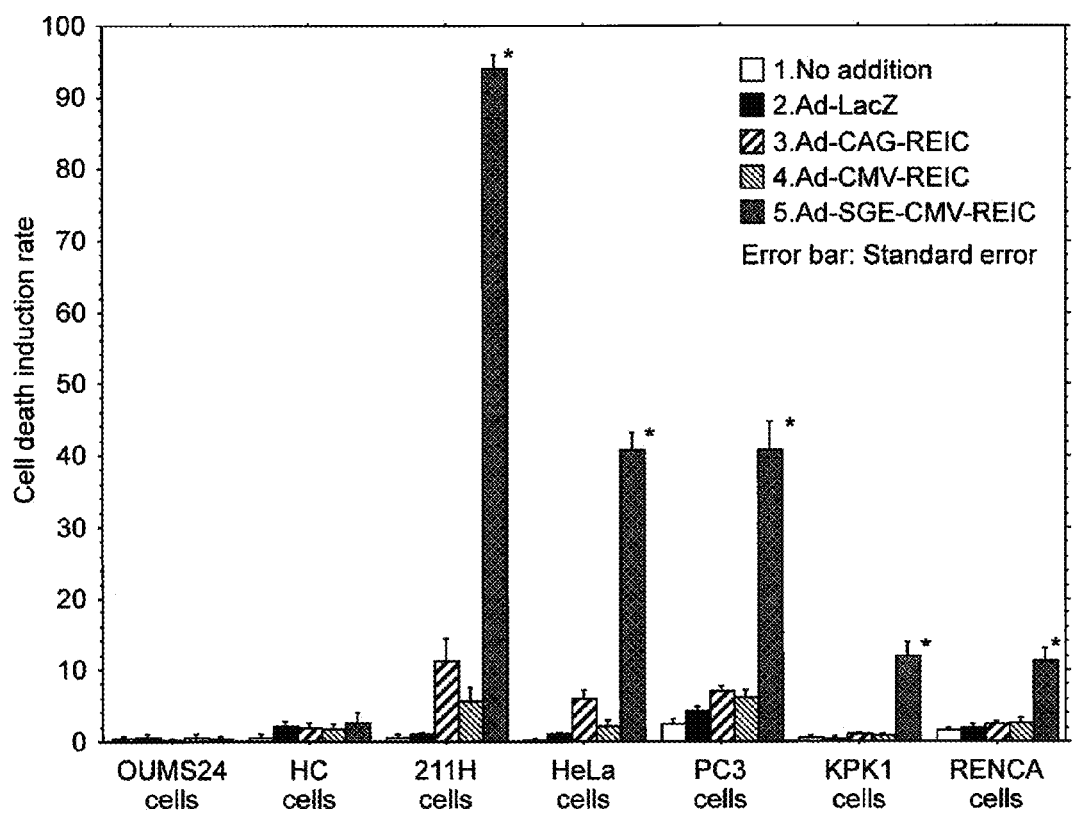
FIG. 8 shows the degrees of cell death induction when various vectors were used.

FIG. 8 shows cell death induction rate (%) for each type of cells resulting from the use of each recombinant adenovirus. As shown in FIG. 8, a significantly higher cell death induction rate (%) was obtained when Ad-SGE-CMV-REIC was used, compared to other recombinant adenoviruses.

Example 5

Tumor Growth-Suppressing Effects of Ad-SGE-CMV-REIC (No. 1)

$2\times10^5$ RENCA cells (mouse kidney cancer-derived cells) were subcutaneously injected to the right femur of female BALB/C mice (6 to 8-week-old) (4 mice per group) on day [−7] (7 days before the initiation of treatment). On day 0, tumors were observed in each mouse. PBS containing 5×10^9 viral particles/100 μL (Ad-SGE-CMV-REIC, Ad-CMV-REIC, or Ad-CAG-REIC) was intratumorally injected on day 0. An adenovirus vector (Ad-LacZ) containing a LacZ gene was used as a control. Also, the same amount of PBS was injected into each negative control mouse. Tumor size was measured once every 2 weeks. Tumor volume was calculated by the formula found by an experiment, "½×(w1×w2×w2)" (where "w1" denotes the greatest tumor dimension, and "w2" denotes the smallest tumor dimension).

Figure 9:
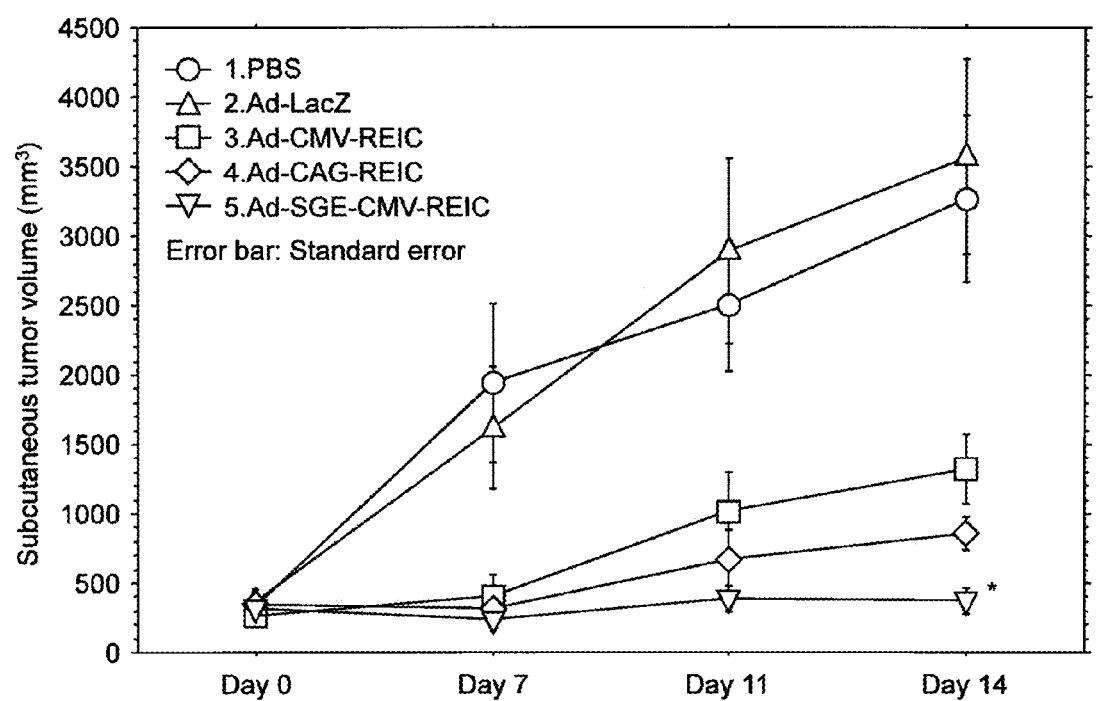
FIG. 9 shows the effects of tumor growth suppression when various vectors were used (No. 1).

The results are shown FIG. 9. As shown in FIG. 9, the Ad-SGE-CMV-REIC treatment group exhibited significantly lower tumor volumes compared to those in the other 4 groups, and thus were confirmed to have the strongest tumor growth-suppressing effects compared to the 4 other groups.

Figure 10:
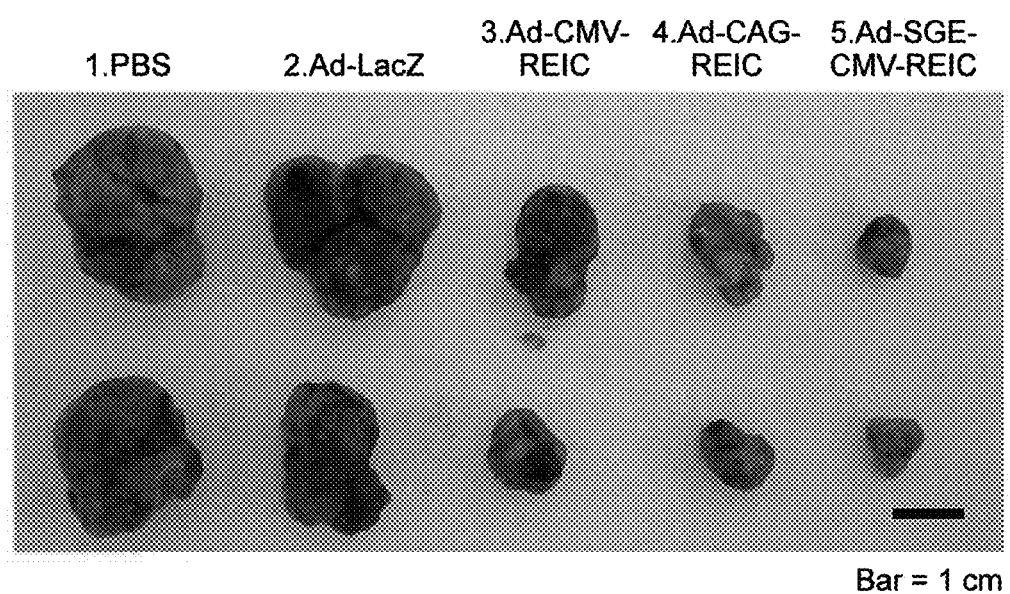
FIG. 10 shows tumors after treatment, indicating tumor growth-suppressing effects when various vectors were used.

Furthermore, subcutaneous tumors were excised on day 14 from each treatment group. Photographs showing typical tumors from two mice (from each treatment group) are shown in FIG. 10. As shown in FIG. 10, the Ad-SGE-CMV-REIC treatment group exhibited significantly lower tumor volumes compared to those of the 4 other groups.

Example 6

Tumor Growth-Suppressing Effects of Ad-SGE-CMV-REIC (No. 2)

2×10^5 RENCA cells (mouse kidney cancer-derived cells) were subcutaneously injected to the right femur of 6 to 8-week-old female BALB/C mice (4 to 5 mice per group) on day [−7] (7 days before the initiation of treatment). Tumors were confirmed in each mouse on day 0. PBS containing 1×10^9 viral particles/100 μl (Ad-SGE-CMV-REIC, Ad-CMV-REIC, or Ad-CAG-REIC) was intratumorally injected on day 0. An adenovirus vector (Ad-LacZ) containing a LacZ gene was used as a control. Also, the same amount of PBS was injected to each negative control mouse. Tumor size was measured once every 2 weeks. Tumor volume was calculated by the formula found by an experiment, "½×(w1×w2×w2)" (where "w1" denotes the greatest tumor dimension, and "w2" denotes the smallest tumor dimension).

Figure 11:
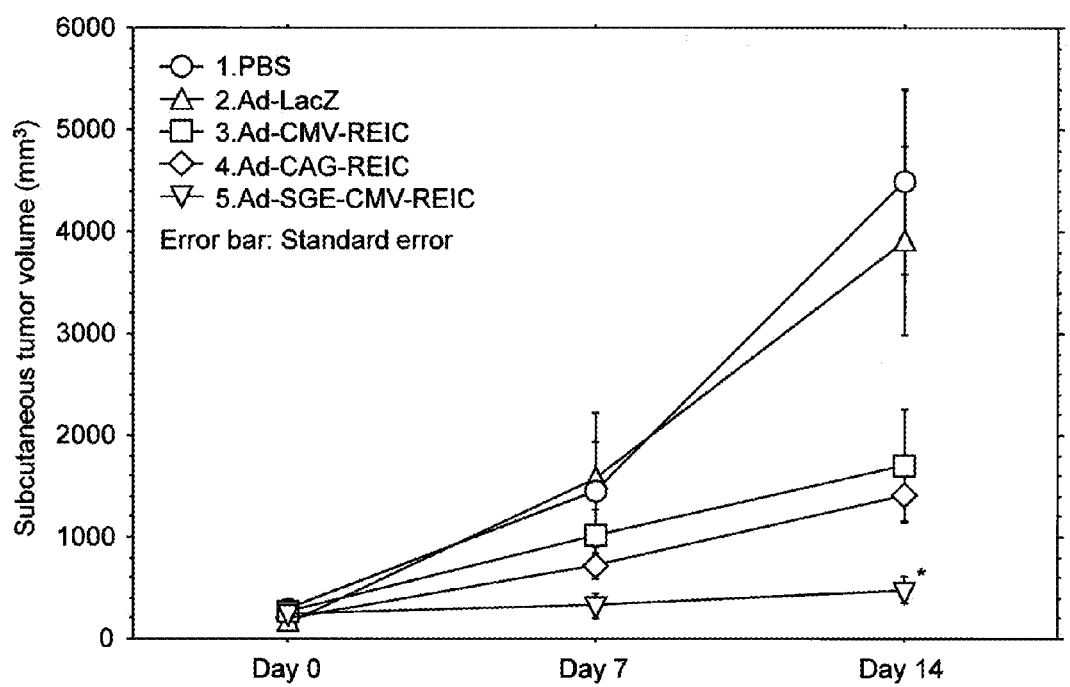
FIG. 11 shows the effects of suppressing tumor growth when various vectors were used (No. 2).

The results are shown in FIG. 11. As shown in FIG. 11, the Ad-SGE-CMV-REIC treatment group exhibited significantly lower tumor volumes compared to those of the 4 other groups, and thus confirmed to have the strongest tumor growth-suppressing effects compared to the 4 other groups.

INDUSTRIAL APPLICABILITY

The adenovirus vector of the present invention containing a DNA construct that contains REIC/Dkk-3 DNA can be used as a cancer therapeutic drug.

Sequence Listing Free Text

SEQ ID NOS: 8 and 9, primers

All publications, patents, and patent applications cited herein are incorporated herein by reference in their entirety.

The invention claimed is:

1. A DNA construct for expression of REIC/Dkk-3 DNA, which is prepared by ligating the following (i) to (iv) in this order, from the 5' terminal side:
   (i) a CMV promoter;
   (ii) the following REIC/Dkk-3 DNA:
      (a) DNA comprising the nucleotide sequence shown in SEQ ID NO: 1, or
      (b) a polynucleotide consisting of SEQ ID NO: 3 or SEQ ID NO: 4;
   (iii) a polyA addition sequence; and
   (iv) enhancers prepared by linking an hTERT (Telomerase Reverse Transcriptase) enhancer, an SV40 enhancer, and a CMV enhancer in this order.

2. The DNA construct according to claim 1, wherein the polyA addition sequence is a polyA addition sequence of bovine growth hormone gene.

3. The DNA construct according to claim 1, containing the nucleotide sequence shown in SEQ ID NO: 6, wherein (ii) the REIC/Dkk-3 DNA, (iii) the polyA addition sequence, and (iv) the enhancers prepared by linking the hTERT (Telomerase Reverse Transcriptase) enhancer, the SV40 enhancer, and the CMV enhancer in this order are ligated.

4. The DNA construct according to claim 1, containing the nucleotide sequence shown in SEQ ID NO: 6.

5. An adenovirus vector, containing the DNA construct according to claim 1.

6. A cancer cell death-inducing agent, containing the adenovirus vector according to claim 5.

7. A tumor cell growth-suppressing agent, containing the adenovirus vector according to claim 5.

8. A cancer therapeutic drug, containing the adenovirus vector according to claim 5.

* * * * *

SEQUENCE LISTING

```
<160> NUMBER OF SEQ ID NOS: 9

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1 atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
  1               5                  10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
             20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
         35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
     50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
 65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                 85                  90                  95 gag acc aac aca gac acg aag gtt gga aat aat acc atc cat gtg cac     336
Glu Thr Asn Thr Asp Thr Lys Val Gly Asn Asn Thr Ile His Val His
            100                 105                 110 cga gaa att cac aag ata acc aac aac cag gct cga caa atg gtc ttt     384
```

```
Arg Glu Ile His Lys Ile Thr Asn Asn Gln Ala Arg Gln Met Val Phe
            115                 120                 125 tca gag aca gtt atc aca tct gtg gga gac gaa gaa ggc aga agg agc      432
Ser Glu Thr Val Ile Thr Ser Val Gly Asp Glu Glu Gly Arg Arg Ser
130                 135                 140 cac gag tgc atc atc gac gag gac tgt ggg ccc agc atg tac tgc cag      480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg      528
Phe Ala Ser Phe Gln Tyr Thr Cys Gln Pro Cys Arg Gly Gln Arg Met
                165                 170                 175 ctc tgc acc cgg gac agt gag tgc tgt gga gac cag ctg tgt gtc tgg      576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt      624
Gly His Cys Thr Lys Met Ala Thr Arg Gly Ser Asn Gly Thr Ile Cys
        195                 200                 205 gac aac cag agg gac tgc cag ccg ggg ctg tgt tgt gcc ttc cag aga      672
Asp Asn Gln Arg Asp Cys Gln Pro Gly Leu Cys Cys Ala Phe Gln Arg
210                 215                 220 ggc ctg ctg ttc cct gtg tgc ata ccc ctg ccc gtg gag ggc gag ctt      720
Gly Leu Leu Phe Pro Val Cys Ile Pro Leu Pro Val Glu Gly Glu Leu
225                 230                 235                 240 tgc cat gac ccc gcc agc cgg ctt ctg gac ctc atc acc tgg gag cta      768
Cys His Asp Pro Ala Ser Arg Leu Leu Asp Leu Ile Thr Trp Glu Leu
                245                 250                 255 gag cct gat gga gcc ttg gac cga tgc cct tgt gcc agt ggc ctc ctc      816
Glu Pro Asp Gly Ala Leu Asp Arg Cys Pro Cys Ala Ser Gly Leu Leu
            260                 265                 270 tgc cag ccc cac agc cac agc ctg gtg tat gtg tgc aag ccg acc ttc      864
Cys Gln Pro His Ser His Ser Leu Val Tyr Val Cys Lys Pro Thr Phe
        275                 280                 285 gtg ggg agc cgt gac caa gat ggg gag atc ctg ctg ccc aga gag gtc      912
Val Gly Ser Arg Asp Gln Asp Gly Glu Ile Leu Leu Pro Arg Glu Val
290                 295                 300 ccc gat gag tat gaa gtt ggc agc ttc atg gag gag gtg cgc cag gag      960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag     1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag         1053
Pro Ala Ala Ala Ala Ala Leu Leu Gly Gly Glu Glu Ile
            340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Val Glu Asp Thr Gln His Lys
    50                  55                  60
```

```
Leu Arg Ser Ala Val Glu Glu Met Glu Ala Glu Ala Ala Lys
 65                  70                  75                  80

Ala Ser Ser Glu Val Asn Leu Ala Asn Leu Pro Pro Ser Tyr His Asn
                 85                  90                  95

Glu Thr Asn Thr Asp Thr Lys Val Gly Asn Asn Thr Ile His Val His
                100                 105                 110

Arg Glu Ile His Lys Ile Thr Asn Asn Gln Ala Arg Gln Met Val Phe
                115                 120                 125

Ser Glu Thr Val Ile Thr Ser Val Gly Asp Glu Gly Arg Arg Ser
130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
                180                 185                 190

Gly His Cys Thr Lys Met Ala Thr Arg Gly Ser Asn Gly Thr Ile Cys
                195                 200                 205

Asp Asn Gln Arg Asp Cys Gln Pro Gly Leu Cys Cys Ala Phe Gln Arg
210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
                260                 265                 270

Cys Gln Pro His Ser His Ser Leu Val Tyr Val Cys Lys Pro Thr Phe
                275                 280                 285

Val Gly Ser Arg Asp Gln Asp Gly Glu Ile Leu Leu Pro Arg Glu Val
                290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
                340                 345                 350

<210> SEQ ID NO 3
<211> LENGTH: 117
<212> TYPE: DNA
<213> ORGANISM: Homo sapiens

<400> SEQUENCE: 3
atgcagcggc ttggggccac cctgctgtgc ctgctactgg cggcggcggt ccccacggcc     60
cccgcgcccg ctccgacggc gacctcggct ccagtcaagc ccggcccggc tctcagc       117

<210> SEQ ID NO 4
<211> LENGTH: 234
<212> TYPE: DNA
<213> ORGANISM: Homo sapiens

<400> SEQUENCE: 4
atgcagcggc ttggggccac cctgctgtgc ctgctactgg cggcggcggt ccccacggcc     60
cccgcgcccg ctccgacggc gacctcggct ccagtcaagc ccggcccggc tctcagctac    120
ccgcaggagg aggccaccct caatgagatg ttccgcgagg ttgaggaact ggtggaggac    180
```

| | | |
|---|---|---|
| acgcagcaca aattgcgcag cgcggtggaa gagatggagg cagaagaagc tgct | | 234 |

<210> SEQ ID NO 5
<211> LENGTH: 262
<212> TYPE: DNA
<213> ORGANISM: Artificial
<220> FEATURE:
<223> OTHER INFORMATION: Synthetic

<400> SEQUENCE: 5

| | |
|---|---|
| tgactgactg acgtttaaac ccgctgatca gcctcgactg tgccttctag ttgccagcca | 60 |
| tctgttgttt gccctcccc cgtgccttcc ttgaccctgg aaggtgccac tcccactgtc | 120 |
| ctttcctaat aaaatgagga aattgcatcg cattgtctga gtaggtgtca ttctattctg | 180 |
| gggggtgggg tggggcagga cagcaagggg gaggattggg aagacaatag caggcatgct | 240 |
| ggggatgcgg tgggctctat gg | 262 |

<210> SEQ ID NO 6
<211> LENGTH: 2355
<212> TYPE: DNA
<213> ORGANISM: Artificial
<220> FEATURE:
<223> OTHER INFORMATION: Synthetic

<400> SEQUENCE: 6

| | |
|---|---|
| tctagagcac catgcagcgg cttggggcca ccctgctgtg cctgctgctg gcggcggcgg | 60 |
| tccccacggc cccgcgccc gctccgacgg cgacctcggc tccagtcaag cccggcccgg | 120 |
| ctctcagcta cccgcaggag gaggccaccc tcaatgagat gttccgcgag gttgaggaac | 180 |
| tgatggagga cacgcagcac aaaattgcgca gcgcggtgga agagatggag cagaagaag | 240 |
| ctgctgctaa agcatcatca gaagtgaacc tggcaaactt acctcccagc tatcacaatg | 300 |
| agaccaacac agacacgaag gttggaaata ataccatcca tgtgcaccga gaaattcaca | 360 |
| agataaccaa caaccagact ggacaaatgg tcttttcaga cagttatc acatctgtgg | 420 |
| gagacgaaga aggcagaagg agccacgagt gcatcatcga cgaggactgt gggcccagca | 480 |
| tgtactgcca gtttgccagc ttccagtaca cctgccagcc atgccggggc cagaggatgc | 540 |
| tctgcacccg ggacagtgag tgctgtggag accagctgtg tgtctggggt cactgcacca | 600 |
| aaatggccac caggggcagc aatgggacca tctgtgacaa ccagagggac tgccagccgg | 660 |
| ggctgtgctg tgccttccag agaggcctgc tgttccctgt gtgcacaccc ctgcccgtgg | 720 |
| agggcgagct ttgccatgac cccgccagcc ggcttctgga cctcatcacc tgggagctag | 780 |
| agcctgatgg agcccttgga cgatgccctt gtgccagtgg cctcctctgc agccccaca | 840 |
| gccacagcct ggtgtatgtg tgcaagccga ccttcgtggg gagccgtgac caagatgggg | 900 |
| agatcctgct gcccagagag gtccccgatg agtatgaagt tggcagcttc atggaggagg | 960 |
| tgcgccagga gctggaggac ctggagagga gcctgactga agatgggcg ctggggagc | 1020 |
| ctgcggctgc cgccgctgca ctgctgggag gggaagagat ttaggggta ccccggctag | 1080 |
| atgactaacg tttaaacccg ctgatcagcc tcgactgtgc cttctagttg ccagccatct | 1140 |
| gttgtttgcc cctcccccgt gccttccttg accctggaag gtgccactcc cactgtcctt | 1200 |
| tcctaataaa atgaggaaat tgcatcgcat tgtctgagta ggtgtcattc tattctgggg | 1260 |
| ggtggggtgg gcaggacag caaggggag gattgggaag acaatagcag gcatgctggg | 1320 |
| gatgcggtgg gctctatggc ggagtactgt cctccgcttc ccacgtggcg gagggactgg | 1380 |

```
ggacccgggc acccgtcctg ccccttcacc ttccagctcc gcctcctccg cgcggacccc    1440
gccccgtccc gacccctccc gggtccccgg cccagccccc tccgggccct cccagccccc    1500 cccccttcctt tccgcggccc cgccctctcc tcgcggcgcg agttttggaa agtccccagg   1560
ctccccagca ggcagaagta tccaaagcat ccatctcaat tagtcagcaa ccaggtgtgg    1620
aaagtcccca ggctccccag caggcagaag tatccaaagc atccatctca attagtcagc    1680
aaccatagtc ccgccctaa ctccgcccat cccgccccta actccgccca gttccgccca     1740
ttctccgccc catggctgac taattttttt tatttatgca gaggccgagg ccgcctctgc    1800
ctctgagcta ttccagaagt agtgaggagg cttttttgga ggccaaggct tttgcaaaaa    1860
gctccgttac ataacttacg gtaaatggcc cgcctggctg accgcccaac gaccccgcc    1920 cattgacgtc aataatgacg tatgttccca tagtaacgcc aatagggact ttccattgac    1980
gtcaatgggt ggagtattta cggtaaactg cccacttggc agtacatcaa gtgtatcata    2040
tgccaagtac gccccctatt gacgtcaata cggtaaatg gcccgcctgg cattatgccc     2100
agtacatgac cttatgggac tttcctactt ggcagtacat ctacgtatta gtcatcgcta    2160
ttaccatggt gatgcggttt tggcagtaca tcaatgggcg tggatagcgg tttgactcac    2220
ggggatttcc aagtctccac cccattgacg tcaatgggag tttgttttgg caccaaaatc    2280
aacgggactt tccaaaatgt cgtaacaact ccgccccatt gacgcaaatg ggcggtaggc    2340
gtgttgccgg aattc                                                    2355

<210> SEQ ID NO 7
<211> LENGTH: 1285
<212> TYPE: DNA
<213> ORGANISM: Artificial
<220> FEATURE:
<223> OTHER INFORMATION: Synthetic

<400> SEQUENCE: 7
gtttaaaccc gctgatcagc ctcgactgtg ccttctagtt gccagccatc tgttgtttgc      60
ccctcccccg tgccttcctt gaccctggaa ggtgccactc ccactgtcct ttcctaataa    120
aatgaggaaa ttgcatcgca ttgtctgagt aggtgtcatt ctattctggg gggtggggtg    180
gggcaggaca gcaaggggga ggattgggaa gacaatagca ggcatgctgg ggatgcggtg    240
ggctctatgg cggagtactg tcctccgctt cccacgtggc ggagggactg gtcctccgct    300
tcccacgtgg cggagggact ggggacccgg gcacccgtcc tgccccttca ccttccagct    360
ccgcctcctc cgcgcggacc ccgccccgtc ccgacccctc ccgggtcccc ggcccagccc    420
cctccgggcc ctcccagccc ctcccccttcc tttccgcggc cccgccctct cctcgcggcg    480
cgagttttgg aaagtcccca ggctccccag caggcagaag tatccaaagc atccatctca    540
attagtcagc aaccaggtgt ggaaagtccc caggctcccc agcaggcaga agtatccaaa    600
gcatccatct caattagtca gcaaccatag tcccgcccct aactccgccc atcccgcccc    660
taactccgcc cagttccgcc cattctccgc cccatggctg actaattttt tttatttatg    720
cagaggccga ggccgcctct gcctctgagc tattccagaa gtagtgagga ggctttttg     780 gaggccaagg cttttgcaaa aagctccgtt acataactta cggtaaatgg cccgcctggc    840
tgaccgccca acgacccccg cccattgacg tcaataatga cgtatgttcc catagtaacg    900
ccaataggga ctttccattg acgtcaatgg gtggagtatt tacggtaaac tgcccacttg    960
gcagtacatc aagtgtatca tatgccaagt acgccccta ttgacgtcaa tgacggtaaa   1020
tggcccgcct ggcattatgc ccagtacatg accttatggg actttcctac ttggcagtac   1080
```

```
atctacgtat tagtcatcgc tattaccatg gtgatgcggt tttggcagta catcaatggg    1140
cgtggatagc ggtttgactc acggggattt ccaagtctcc accccattga cgtcaatggg    1200
agtttgtttt ggcaccaaaa tcaacgggac tttccaaaat gtcgtaacaa ctccgcccca    1260
ttgacgcaaa tgggcggtag gcgtg                                          1285

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
atgagacata ttatctgcca c                                              21

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
gtaagtcaat cccttcctgc ac                                             22
```